(12) United States Patent
Tower, III et al.

(10) Patent No.: US 9,513,248 B2
(45) Date of Patent: Dec. 6, 2016

(54) POTENTIOMETRIC SENSOR

(71) Applicant: Invensys Systems Inc., Foxboro, MA (US)

(72) Inventors: Daniel G. Tower, III, Wrentham, MA (US); Steven J. West, Hull, MA (US); Michael Mason Bower, Wareham, MA (US); Jose L. Pestana, Plymouth, MA (US); Zhisheng Sun, Hopkinton, MA (US); Stephen B. Talutis, Milton, MA (US)

(73) Assignee: Invensys Systems, Inc., Foxboro, MA (US)

( * ) Notice: Subject to any disclaimer, the term of this patent is extended or adjusted under 35 U.S.C. 154(b) by 586 days.

(21) Appl. No.: 14/041,715

(22) Filed: Sep. 30, 2013

(65) Prior Publication Data

US 2014/0090978 A1    Apr. 3, 2014

Related U.S. Application Data

(60) Provisional application No. 61/708,009, filed on Sep. 30, 2012.

(51) Int. Cl.
| | | |
|---|---|---|
| *G01N 27/36* | (2006.01) | |
| *G01N 27/403* | (2006.01) | |
| *G01N 27/30* | (2006.01) | |

(52) U.S. Cl.
CPC ............ *G01N 27/302* (2013.01); *G01N 27/36* (2013.01); *G01N 27/4035* (2013.01)

(58) Field of Classification Search
CPC ... G01N 27/333; G01N 27/36; G01N 27/4035
See application file for complete search history.

(56) References Cited

U.S. PATENT DOCUMENTS 3,617,460 A * 11/1971 Krull .................. G01N 27/3335
204/417
4,252,124 A * 2/1981 Maurer ................ A61B 5/0448
204/420

* cited by examiner

*Primary Examiner* — Alexander Noguerola
(74) *Attorney, Agent, or Firm* — Stephen Manetta; Ralph Graham

(57) ABSTRACT

A potentiometric sensor includes an elongate non-glass, non-metal housing having opposite first and second longitudinal ends and a length extending between the first and second longitudinal ends. The housing defines a lumen extending along the length of the housing. A measuring half-cell assembly is received in the lumen of the housing and secured to the housing. The measuring half-cell assembly includes a glass body having opposite first and second longitudinal ends and a length extending between the first and second ends of the glass body. The second longitudinal end of the glass body is adjacent the second longitudinal end of the housing and a longitudinal extent of the glass body is less than the length of the housing.

17 Claims, 9 Drawing Sheets

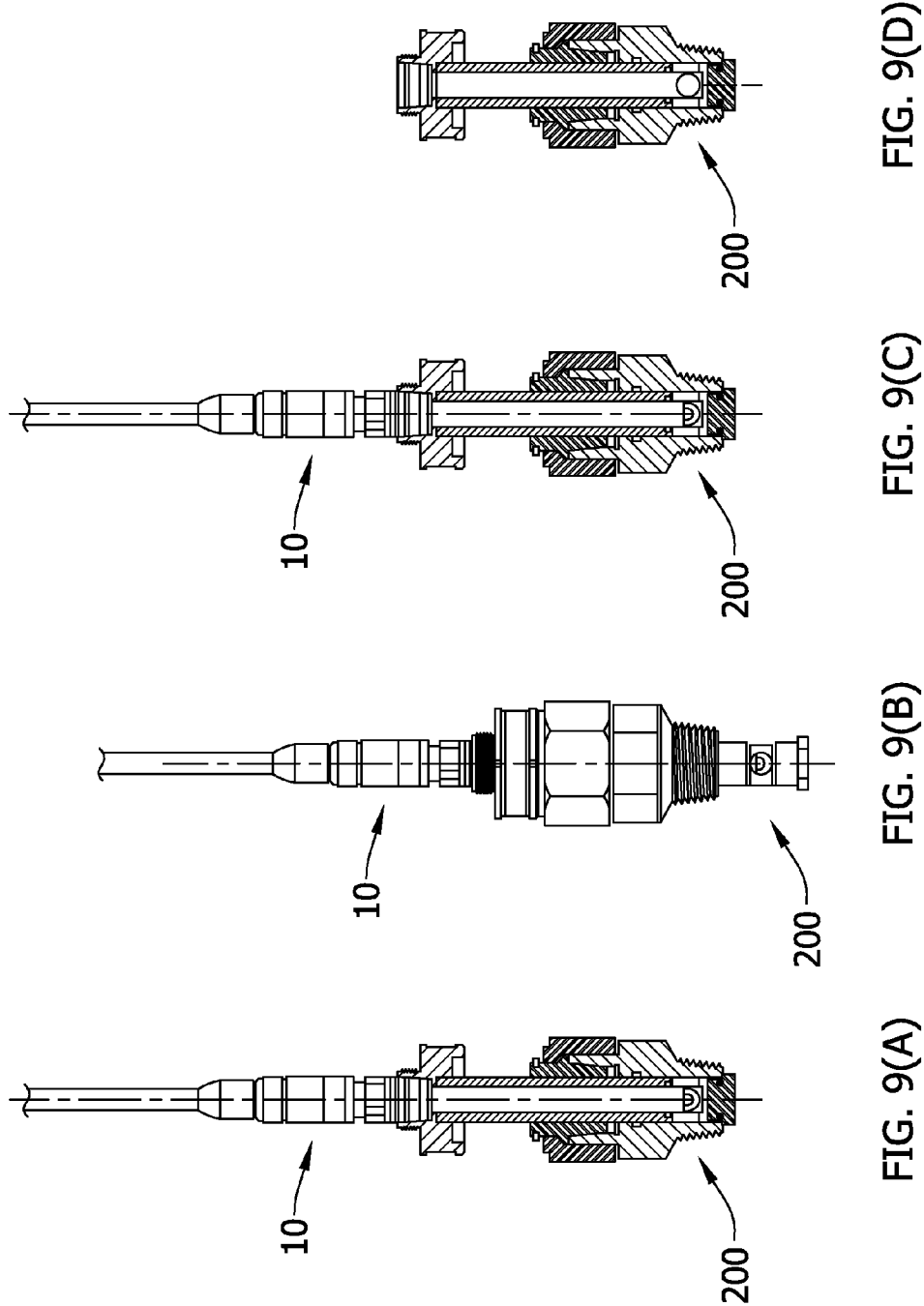

POTENTIOMETRIC SENSOR

CROSS REFERENCE TO RELATED APPLICATIONS

This application claims priority from U.S. Provisional Application No. 61/708,009, filed on Sep. 30, 2012.

FIELD OF THE DISCLOSURE

The present disclosure generally relates to a potentiometric sensor.

BACKGROUND OF THE DISCLOSURE

Electrochemical potential measurements are commonly used to determine solution pH, other selective ion activities, ratios of oxidation and reduction activities, as well as other solution characteristics. A pH/ion selective electrode/oxidation reduction potential meter (hereafter referred to as a pH/ISE/ORP meter) is typically a modified voltmeter that measures the electrochemical potential between a reference half-cell (of known potential) and a measuring half-cell. These half-cells, in combination, form a cell, the electromotive force (emf) of which is equal to the algebraic sum of the potentials of the two half-cells. The meter is used to measure the total voltage across the two half-cells. The potential of the measuring half-cell is then determined by subtracting the known potential of the reference half-cell from the total voltage value.

The measuring half-cell typically includes an ion selective material such as glass. The potential across the ion selective material is well known by those of ordinary skill in the art to vary in a manner that may generally be described by the Nernst Equation, which expresses the electrochemical potential as a logarithmic function of ion activity (thermodynamically corrected concentration). A pH meter is one example of a pH/ISE/ORP meter wherein the activity of hydrogen ions is measured. The definition of pH is the negative logarithm of the hydrogen ion activity and is typically proportional to the measured electrochemical potential.

One example of a pH/ISE/ORP meter is disclosed in U.S. Published Application No. 2011/0048971, filed Aug. 26, 2010 the contents of which are incorporated by reference in their entirety. This meter includes an elongate outer housing having first and second longitudinal ends. The outer housing may be formed from glass. A measuring half-cell received in the outer housing includes a stem glass tube extending along the length of the outer housing from adjacent the first end to adjacent the second end, and a pH glass membrane connected to the end of the stem glass tube adjacent the second end of the outer housing. A solution ground assembly received in the outer housing includes an electrical conductor received in a tubular non-electrically conductive sleeve extending along the length of the housing from adjacent the first end to adjacent the second end of the outer housing. Longitudinal end margins of the stem glass housing and the non-electrically conductive sleeve of the solution ground assembly are received in and generally fixedly secured to respective first and second seals adjacent to the corresponding first and second longitudinal ends of the outer housing. The first and second seals are generally fixedly secured in the outer housing.

SUMMARY OF THE INVENTION

In one aspect, the present invention includes a potentiometric sensor comprising an elongate non-glass, non-metal housing having opposite first and second longitudinal ends and a length extending between the first and second longitudinal ends. The housing defines a lumen extending along the length of the housing. A measuring half-cell assembly is received in the lumen of the housing and secured to the housing. The measuring half-cell assembly includes a glass body having opposite first and second longitudinal ends and a length extending between the first and second ends of the glass body. The second longitudinal end of the glass body is adjacent the second longitudinal end of the housing, and a longitudinal extent of the glass body is less than the length of the housing.

In some embodiments, the longitudinal extent of the glass body is less than three-quarters the length of the housing.

In certain embodiments, the longitudinal extent of the glass body is less than one-half the length of the housing.

In certain embodiments, the longitudinal extent of the glass body is less than one-third the length of the housing.

In certain embodiments, the longitudinal extent of the glass body is less than one-fourth the length of the housing.

In some embodiments, the glass body is secured to the housing at a single longitudinal portion of the glass body so that the glass body generally moves with the housing during thermal linear expansion of the housing.

In some embodiments, the measuring half-cell assembly further includes a lead wire extending through the lumen to the glass body, a reference wire within the glass body, and a seal in the glass body. The lead wire and the reference wire are electrically connected in the seal.

In some embodiments, the sensor is at least partially bendable along a longitudinal portion that does not include the glass body.

In some embodiments, the housing comprises a plastic material.

In another aspect of the present invention, a potentiometric sensor comprises an elongate non-glass, non-metal housing having opposite first and second longitudinal ends and a length extending between the first and second longitudinal ends. The housing defines a lumen extending along the length of the housing. A measuring half-cell assembly is received in the lumen of the housing. The measuring half-cell assembly includes a glass body having opposite first and second longitudinal ends and a length extending between the first and second ends of the glass body. The glass body is secured to the housing at a single longitudinal portion of the glass body so that the glass body generally moves with the housing during thermal linear expansion of the housing.

In some embodiments, a first seal is adjacent the first longitudinal end of the housing for inhibiting the ingress and egress of fluid into and out the lumen.

In certain embodiments, a second seal is spaced apart from the first seal along the length of the housing. The second seal is positioned at the single longitudinal portion of the glass body for inhibiting the ingress and egress of fluid into and out the lumen and securing the housing to the single longitudinal portion of the glass body.

In certain embodiments, the first end of the glass body is free from securement to the first seal and is spaced apart from the first seal along the length of the housing.

In certain embodiments, the second seal comprises an electrically conductive end cap. The end cap is electrically connected to a wire and a process fluid.

In some embodiments, the measuring half-cell assembly further includes a lead wire extending through the lumen to the glass body, a reference wire within the glass body, and a seal in the glass body. The lead wire and the reference wire are electrically connected in the seal.

In some embodiments, the sensor further comprises a solution ground assembly and a heat shrinking tube. The heat shrinking tube is disposed around a portion of the glass body and a portion of the solution ground assembly to hold said portion of the glass body in place with respect to said portion of the solution ground assembly.

In another embodiment, the present invention includes a potentiometric sensor comprising an elongate non-glass, non-metal housing having opposite first and second longitudinal ends and a length extending between the first and second longitudinal ends. The housing defines a lumen extending along the length of the housing. A first seal is adjacent the first longitudinal end of the housing for inhibiting the ingress and egress of fluid into and out the lumen. A second seal is spaced apart from the first seal along the length of the housing. The second seal is adjacent the second longitudinal end of the housing for inhibiting the ingress and egress of fluid into and out of the lumen. A measuring half-cell assembly received in the lumen of the housing. The measuring half-cell assembly includes a glass body having opposite first and second longitudinal ends and a length extending between the first and second ends of the glass body that is less than the length of the housing. The measuring half-cell assembly further includes a lead wire extending through the lumen to the glass body, a reference wire within the glass body, and a seal in the glass body. The lead wire and the reference wire being electrically connected in the seal.

In some embodiments, the second longitudinal end of the glass body is adjacent the second longitudinal end of the housing and a longitudinal extent of the glass body is less than the length of the housing.

In certain embodiments, the glass body is secured to the housing at a single longitudinal portion of the glass body so that the glass body generally moves with the housing during thermal linear expansion of the housing.

In some embodiments, the seal in the glass body comprises longitudinally spaced first and second seals and electrically non-conductive material disposed between the first and second seals. The lead wire and the reference wire are electrically connected in the non-conductive material.

Other aspects and embodiments of the present invention will be apparent in view of the following description and claims.

BRIEF DESCRIPTION OF THE DRAWINGS

FIG. 9(a) is a partial section showing the potentiometric sensor being inserted into an insertion assembly;

FIG. 9(b) is an elevation showing the potentiometric sensor fully installed in the insertion assembly;

FIG. 9(c) is a partial section showing the potentiometric sensor retracted into the insertion assembly; and, FIG. 9(d) is a section of the connector assembly.

Corresponding reference characters indicate corresponding parts throughout the drawings.

DETAILED DESCRIPTION OF THE DRAWINGS

Figure 1:
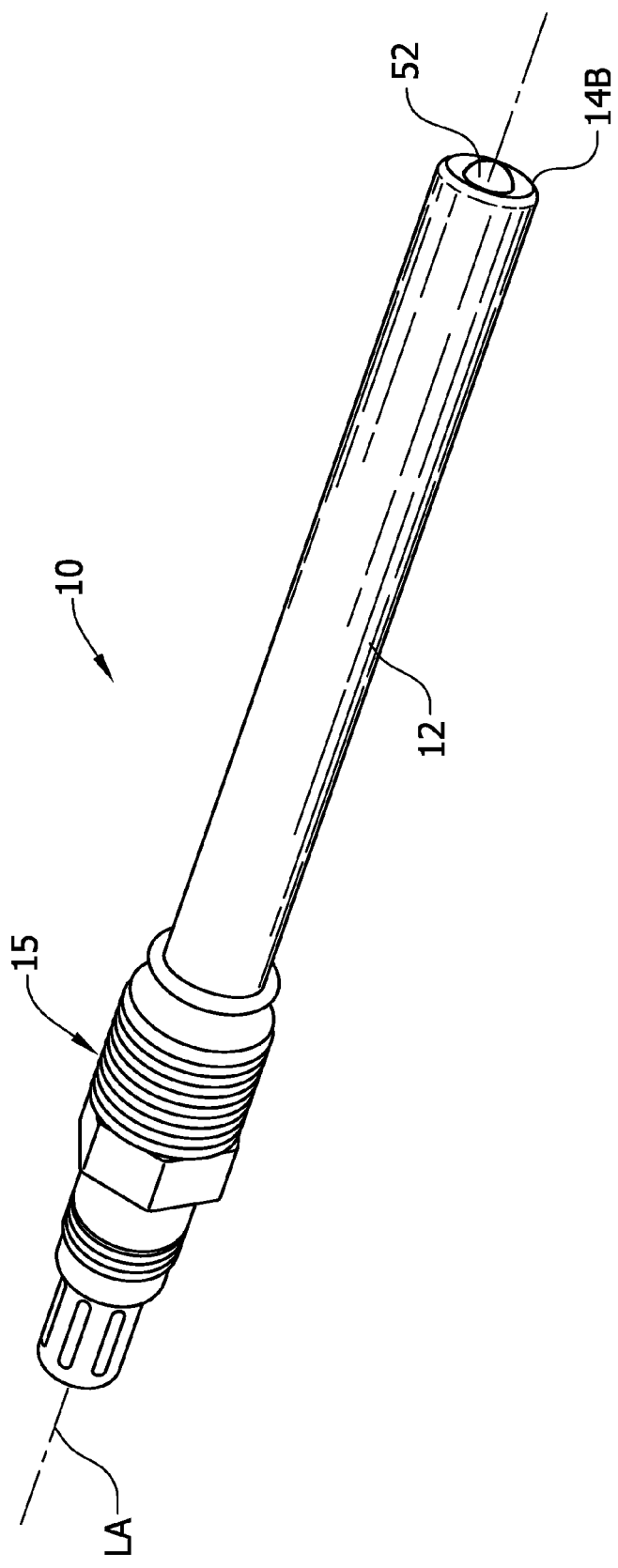
FIG. 1 is a perspective of a potentiometric sensor.

Referring now to the drawings, an embodiment of a potentiometric sensor is generally indicated at reference numeral 10. The sensor 10 includes an elongate non-glass, non-metal housing 12 having opposite first and second ends 14A, 14B, and a longitudinal axis LA extending therebetween. The housing 12 defines a reference electrolyte lumen 16 extending along the longitudinal axis LA of the housing. A suitable connector assembly, generally indicated at 15, is secured to the first end 14A of the housing 12 and defines a wire collection chamber 15A (FIG. 3) adjacent to the first end 14A of the housing 12. The structure and function of the connector assembly 15 is generally known in the art, and therefore, it is not described in detail. The sensor 10 may include a different type of connector assembly or may not include a connector assembly without departing from the scope of the present invention. As explained in more detail below, disposed within the reference electrolyte lumen 16 are a measuring half-cell assembly, generally indicated at 20, including a glass body 48; a solution ground assembly, generally indicated at 22; a reference half-cell assembly, generally indicated at 24; and a pressure equalization bladder 26. It is understood that the sensor 10 may include other components not illustrated, or the sensor may not include some of the illustrated components, without departing from the scope of the present invention. The illustrated sensor 10 is suitable for the measurement of pH, since pH is a commonly measured analyte. However, it should be understood that the sensor 10 may configured as sensor for other measurements, including but not limited to ORP, fluoride ion detection, or other ion-selective measurements.

As disclosed above, the housing 12 is a non-glass, non-metal component, meaning that the housing is formed from a material other than glass and metal. In one embodiment, the housing 12 is formed from a plastic material, although the housing may be formed from a material other than plastic. Examples of suitable plastics may include any number of structurally rugged, chemically inert materials, such as PEEK (polyetheretherketone), Ryton® PPS (polyphenylene sulfide, Chevron Phillips Chemical Company), or Kynar® (PVDF). In various embodiments, these polymeric materials may provide the desired resistance to breakage, while also providing sufficient structural rigidity to protect relatively fragile interior components such as the measuring half-cell assembly 20, from damage both during use and during installation and removal from the process. In one example, the housing 12 has a flexural modulus greater than the glass body 48 of the measuring half-cell assembly 20.

The outer housing 12 may be generally cylindrical, with a predetermined length and diameter that may be suitable for a particular industry. In one example, the outer diameter of the outer housing 12 may be 12 mm, keeping with an industry standard. The length L1 (FIG. 3) of the outer housing 12 may be 120 mm or greater. In one embodiment, the length L1 is greater than 120 mm, and in one example, the length L1 may measure 225 mm, 360 mm, or 425 mm, keeping with industry standards. The length L of the outer housing 12 may have other dimensions without departing from the scope of the present invention.

As is generally known by those of ordinary skill, the reference electrolyte lumen 16 of the housing 12 is at least partially filled with a reference electrolyte solution, including but not limited to a solution including potassium chloride, silver chloride, and combinations thereof. One particular example includes a mixture of about 4 molar potassium chloride and saturated silver chloride. The reference electrolyte may take the form of a conventional gelled electrolyte. It should be recognized that gelled electrolytes tend to provide for relatively slow diffusion, which advantageously tends to slow electrolyte contamination during use. The conductive (optionally gelled) electrolyte in the reference electrolyte lumen 16 surrounds the measuring half-cell assembly 20 to effectively shield it from electromagnetic radiation.

The electrolyte solution is sealed within the reference electrolyte lumen 16 by two internal plugs or seals: a first seal 30A adjacent to the first end 14A of the housing 12; and a second seal 30B adjacent to the second end 14B. As explained below, the first and second seals 30A, 30B are generally fixedly secured (such as by friction or press-fit) within the reference electrolyte lumen 16, and the measuring half-cell assembly 20 and the solution ground assembly 22 are generally fixedly secured to the second seal 30B to generally fix the position of the measuring half-cell assembly and the solution ground assembly relative to the housing. The first and second seals 30A, 30B may be fabricated from plastic, elastomeric, or other suitable electrically non-conductive and chemically inert resilient materials. Examples of suitable materials include various elastomers such as silicone rubber, EPDM, fluoroelastomers such as VITON® (DuPont), and perfluoroelastomers such as Kalzrez™ or Chemraz™ may be chosen for their mechanical and chemical properties. Polymers such as PTFE, PFA, or PEEK may also be used, with or without elastomeric O-rings.

Figure 2:
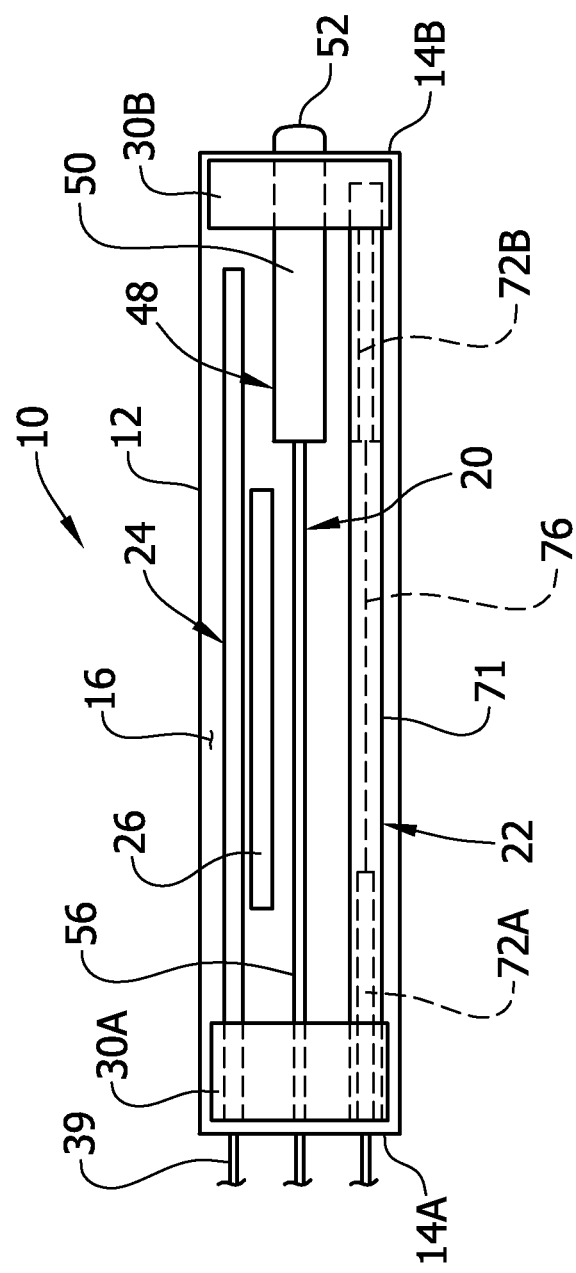
FIG. 2 is a schematic elevation of the sensor, with a connector assembly of the sensor removed.
Figure 4:
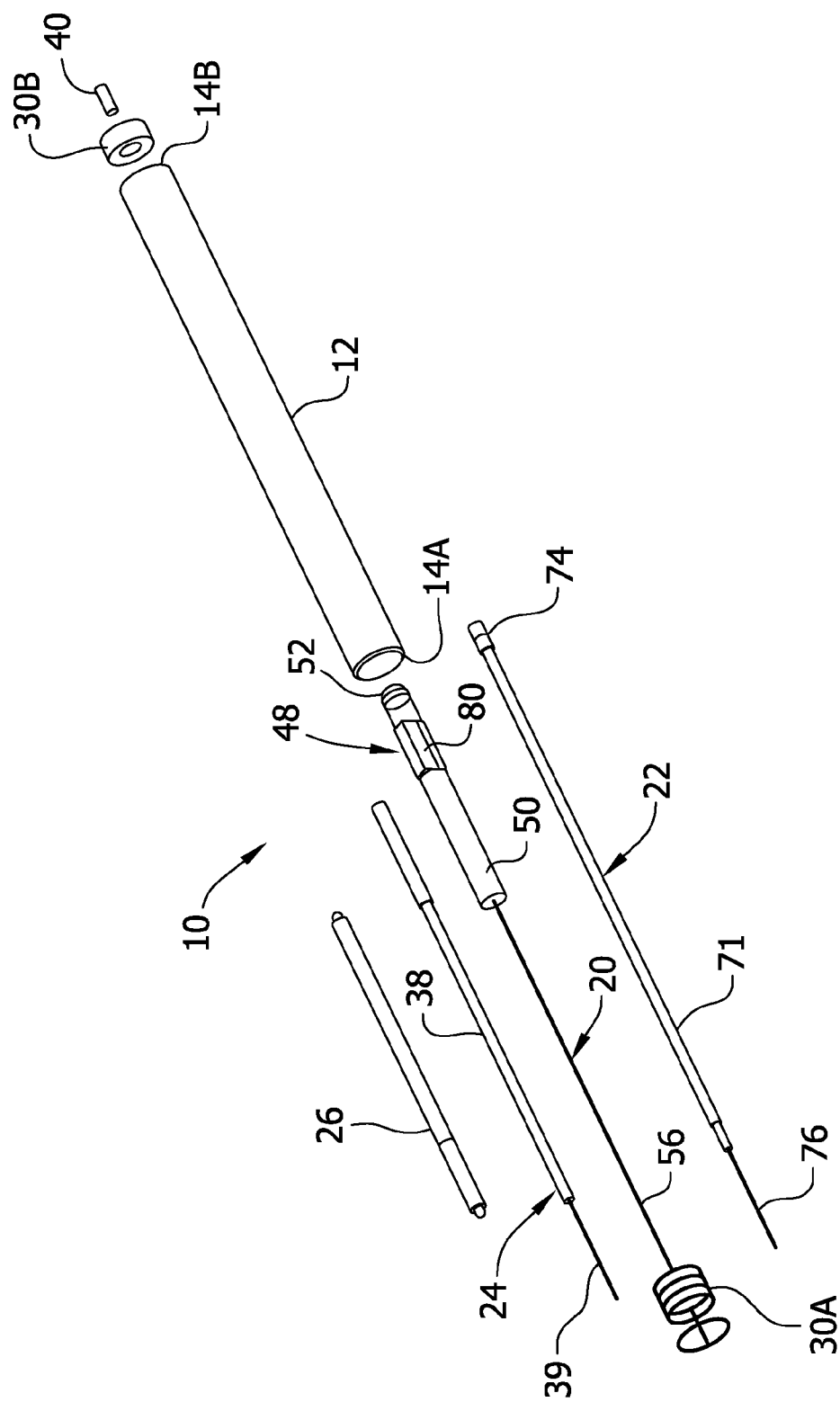
FIG. 4 is an exploded perspective of the sensor, with the connector assembly removed.

Referring to FIGS. 2 and 4, the reference half-cell assembly 24 may be of a configuration generally known in the art. For example, the reference half-cell assembly 24 may include a reference electrode (e.g., silver, silver-silver chloride, mercury-mercurous sulfate, mercury-mercurous chloride, other redox couples, and other suitable material) encased in a polymer tube 38, and a reference lead wire 39 extending through the first seal 30A and into the wire collection chamber 15A in the connector assembly 15. In one example, the reference half-cell assembly tube 38 may be made of NAFION® (DuPont). Those skilled in the art will recognize that NAFION® is a permselective polymer that prevents complex silver anions in the reference half-cell assembly 24 from entering the reference electrolyte in the reference electrolyte lumen 16. As shown in FIG. 4, a liquid junction 40 (or reference junction) is received in a longitudinal opening in the second seal 30B. The liquid junction 40 includes an ion barrier, e.g., in the form of a porous member configured to provide controlled flow of the reference electrolyte in the reference electrolyte lumen 16 therein to form a primary electrical pathway extending through the liquid junction.

The pressure compensator (or pressure equalization bladder) 26 may be of a configuration generally known in the art. The compensator 26 is configured to expand or contract in response to relatively low or high external pressures on the housing 12, to help compensate for pressure variations in the test (process) fluid. In particular embodiments, the pressure compensator 26 may take the form of a sealed, gas (e.g., air)—filled polymeric tube. The gas may thus compress when subjected to higher pressure from the process, or due to thermal expansion of the reference electrolyte in the reference electrolyte lumen 16. This compression may help guard against components rupturing or the seals 30A, 30B or liquid junction 40 being blown out of the housing 12.

Figure 3:
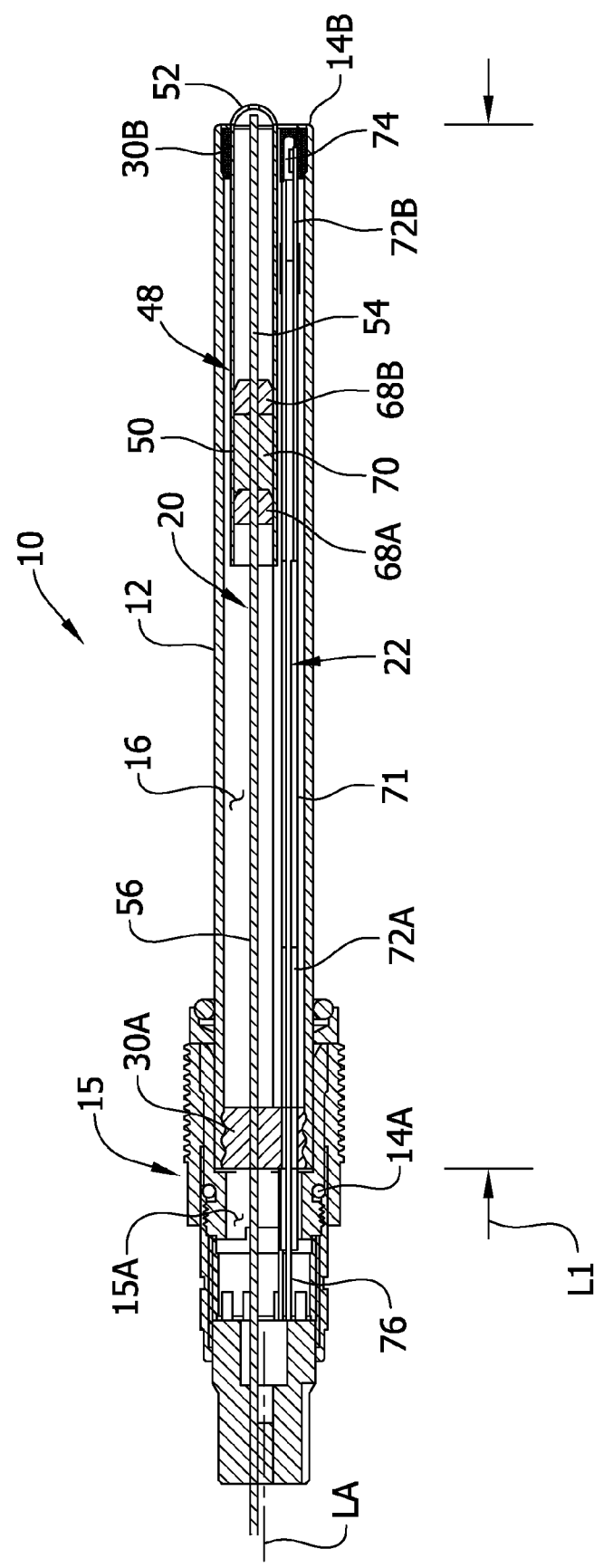
FIG. 3 is a longitudinal section of the sensor of FIG. 1.
Figure 5:
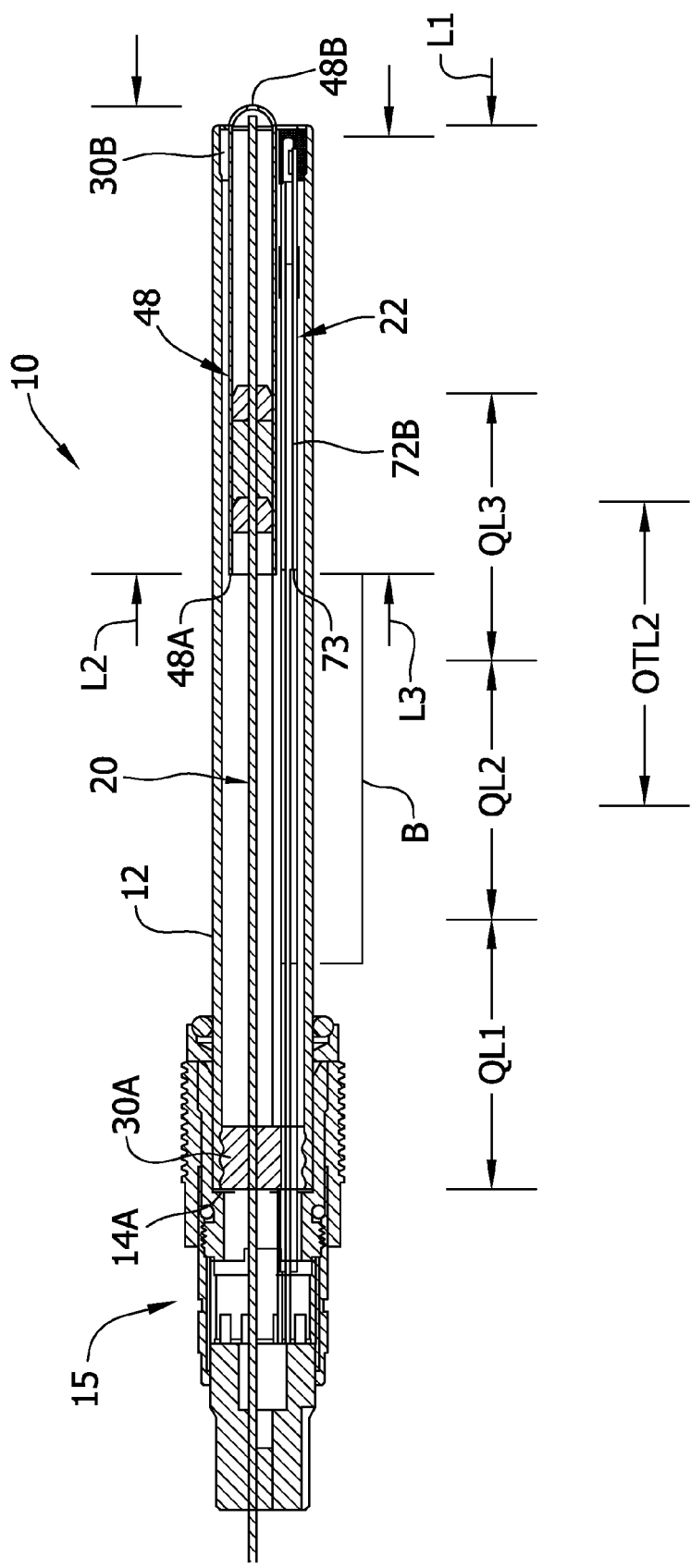
FIG. 5 is longitudinal section of the sensor similar to FIG. 3.

Referring to FIGS. 3-5, the measuring half-cell assembly 20 generally includes a glass body, generally indicated at 48, having opposite first and second longitudinal ends 48A, 48B. The glass body 48 includes a stem glass tube 50 (e.g., an inert glass tube), and a glass membrane 52 (e.g., a pH-sensitive glass membrane) at the second end 48B of the glass body secured to stem glass tube 50. A lumen 53 (FIG. 6) defined by the glass body 48 is at least partially filled with an electrolyte solution. A reference wire 54 is immersed in the electrolyte solution and extends longitudinally within the stem glass tube 50 and into the glass membrane 52. As explained in more detail below, a lead wire 56 is electrically connected to the reference wire 54 and extends toward the first end 14A of the housing body 12, through the first seal 30A and into the wire collection chamber 15A of the connector assembly 15.

Figure 6:
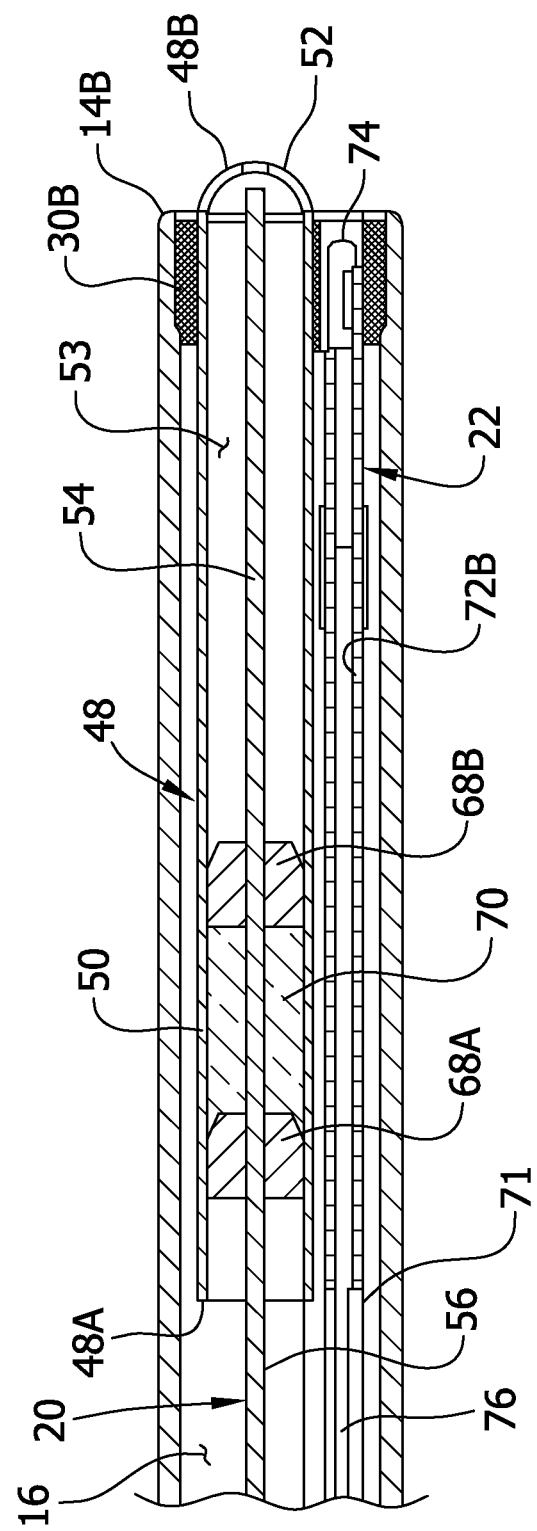
FIG. 6 is an enlarged, fragmentary view of FIG. 3.

As shown best in FIG. 6, the second end margin of the glass body 48 is generally fixedly received in a longitudinal opening in the second seal 30B securing the second end 48B of the measuring half-cell assembly to the housing 12. At least a portion of the glass membrane 52 extends through the second seal (and through the second end 14B of the housing 12) for exposure to the process fluid. In the illustrated embodiment, the first end 48A of the glass body 48 is free from securement to the first seal 30A and is spaced apart from the first seal along the length of the housing 12. Because the glass body 48 is secured to the housing 12 at only one end (e.g., at its second end 48B and not its first end 48A), the glass body is able to move longitudinally with the second end 14B of the housing during thermal expansion of the housing, without undergoing longitudinal strain (e.g., tensile strain) due to the thermal expansion (e.g., elongation) of the housing. The benefit of this feature is apparent when analyzing a sensor that includes a glass body of a measuring half-cell assembly fixedly secured at both of its ends to a non-glass, non-metal housing having a coefficient of linear thermal expansion that is much greater (e.g., greater by a magnitude of 5) than the glass body. When the sensor is heated to certain high temperatures, such as during sterilization, the housing undergoes more linear thermal expansion than the glass body. Because both ends of the glass body are fixedly secured to the housing, linear thermal expansion of the housing will impart linear stresses (e.g., tensile stress) on the glass tube, leading to linear strain (e.g., tensile strains) of the glass tube and possible failure (i.e., breakage). In such a sensor, the glass body is more likely to fail due to thermal linear expansion of the housing when one or more (and possibly others) of the following variable increases: 1) the temperature at which the sensor is exposed; 2) the ratio of the housing's coefficient of linear thermal expansion to the glass body's coefficient of linear thermal expansion; and 3) and the length of the housing. Accordingly, the benefits derived from fixedly securing only one end (e.g., the second end 48B) of the glass body 48 to the housing 12 are even more apparent in a disclosed embodiment of the present invention where 1) the housing is plastic (e.g., PEEK), 2) the measuring half-cell body 48 is glass, 3) the sensor is exposed to high temperatures, and 4) the length of the housing is greater than 120 mm (e.g., 225 mm, 360 mm, or 425 mm).

Referring FIG. 5, in one embodiment, a length L2 of the glass body 48 is less than the length L1 of the housing 12, and in particular, the longitudinal extent of the glass body is less than the full length of the housing. By making the glass body 48 shorter than the housing 12, the glass body is less likely to fail (i.e., break) due to flexural or bending strain induced by flexural or bending stresses imparted on the sensor 10. In fact, the shorter the glass body is, the less likely the glass body will fail to due bending stresses on the sensor 10. In typical situations, bending stresses may be imparted on the sensor 10, particularly longer sensors (e.g., greater than 120 mm) if the sensor is dropped, when the sensor is inserted into the process, etc. Accordingly, shortening the glass body 48 so that it is shorter than the length of the housing makes the sensor more robust and less likely to break. In addition, the sensor 10 is at least partially bendable at a longitudinal portion B of the sensor that does not include the glass body 48.

Referring to FIG. 5, in one example, the longitudinal extent of the glass body is less than ¾ the length L1 of the housing 12. In other words, the first end 48A of the glass body 48 does not extend to (i.e., is spaced apart longitudinally from) a first quarter-length QL1 of the housing 12 as measured from the first longitudinal end 14A of the housing. In another embodiment, the longitudinal extent of the glass body 48 is less than ½ the length L1 of the housing 12. In other words, the first end 48A of the glass body 48 does not extend to (i.e., is spaced apart longitudinally from) a second quarter-length QL2 (i.e., mid-length) of the housing 12 as measured from the first longitudinal end 14A of the housing. In yet another embodiment, the longitudinal extent of the glass body 48 is less than or equal to ⅓ the length of the housing 12. In other words, the first end 48A of the glass body 48 does not extend to (i.e., is spaced apart longitudinally from) a second one-third length OTL2 of the housing 12 as measured from the first longitudinal end 14A of the housing. In another embodiment, the longitudinal extent of the glass body 48 is less than ¼ the length L1 of the housing 12. In other words, the first end 48A of the glass body 48 does not extend to (i.e., is spaced apart longitudinally from) a third quarter-length QL3 of the housing 12 as measured from the first longitudinal end 14A of the housing.

Because the length L2 of the glass body 48 of the illustrated embodiment is shortened and does not extend through the first seal 30A, interior lumen 53 of the glass body and the electrolyte solution contained therein are sealed and insulated from the reference electrolyte solution in the reference electrolyte lumen 16 of the housing 12 separately from the first seal. Referring to FIG. 6, in the illustrated embodiment, the measuring half-cell assembly 50 includes longitudinally spaced first and second seals 68A, 68B in the interior space of the glass body. The lead wire 56 and the reference wire 54 are electrically connected (e.g., soldered) in a junction area between the seals 68A, 68B, and the junction area is potted with an electrically non-conductive material 70 (e.g., thermo-setting plastics or silicone rubber). The reference wire 54 extends through the second seal 68B into the junction area. The lead wire 56 extends from the junction area, through the first seal 68A and into the reference electrolyte solution. As shown in FIG. 3, the lead wire 56 extends through the first seal 30A and into the connector 15. Because the lead wire 56 extends through the reference electrolyte solution in the reference electrolyte lumen 16, the wire includes an electrical insulation sleeve. For example, the lead wire 56 may be insulated from the reference electrolyte solution with a PTFE sleeve covering the wire. In one embodiment, the first and second seals 68A, 68B are fluoropolymer elastomers (e.g., Viton® from DuPont Performance Elastomers LLC), and the potting 70 between the first and second seals is KPPU. In one embodiment, the reference and lead wires 54, 56, respectively, are electrically insulated from the reference electrolyte at a resistance of $10^{12}$ ohms.

Referring to FIGS. 3 and 4, the solution ground assembly 22 extends along the length L1 of the housing 12 from the second seal 30B through the first seal 30A. The solution ground assembly 22 includes an electrically non-conductive outer jacket or sleeve 71, spaced apart first and second electrically conductive tubes 72A, 72B (e.g., stainless steel tubes) in the sleeve adjacent respective first and second ends of the sleeve, an electrically and thermally conductive metallic or non-metallic end cap 74 received in a longitudinal cavity of the second seal 30B, and at least one wire 76 electrically connected to the cap and extending through the first and second conductive tubes and into the wiring collection chamber 15A of the connector 15. The end cap 74 may be electrically conductive, but non-metallic, to serve as a solution ground contact. The end cap 74 may be fabricated from any number of electrically conductive, non-metallic materials known to those skilled in the art. In particular embodiments, the end cap 74 may be fabricated from polyvinylidene fluoride, due to its wide applicability to various applications and its general acceptance by users in the field of electrochemical sensing.

The solution (process fluid) ground contact, such as provided by end cap 74, may be used to provide a reference potential that may be subtracted from the potentials provided by measuring and reference half-cell assemblies 20, 24, respectively. Such use may effectively prevent variable, spurious currents and potentials in the process fluid from interfering with the measured pH signal. In addition, the solution ground contact 74 may enable useful diagnostics when the readout instrumentation has such capabilities. For example, monitoring the electrical resistance between the ground contact 74 and the measuring half-cell lead wire 56 may indicate a break or crack in the glass membrane 52. Likewise, monitoring the resistance of the liquid junction 40 may have diagnostic value.

The end cap 74 may also serve another purpose. If the end cap 74 is fabricated from an inert metal, such as platinum, it may serve as an ORP sensing half-cell. In such an embodiment, the sensor 10 becomes a multi-measurement device capable of measuring pH and ORP simultaneously when connected to an appropriately configured electrometer.

Further, the solution ground assembly 22 may serve as a housing for a temperature sensor (not shown) in the form of an RTD or other element, e.g., disposed within end cap 74, to thus serve as a combination solution ground and RTD assembly. This configuration brings the RTD relatively close to the process fluid, with separation provided by the end cap 74 with relatively good heat conducting properties. Moreover, the temperature sensor may be thermally isolated from the thermal mass of the probe by embedding it in the weakly heat-conducting second seal 30B, while it is thermally coupled to the process fluid by means of the end cap 74 being a thin-walled and relatively strongly heat-conducting.

In the illustrated embodiment, the second electrically conductive tube 72B has a length L3 is less than a length L2 of the housing 12, and in particular, the longitudinal extent of the second conductive tube relative to the housing is less than the full length of the housing (FIG. 5). In the illustrated embodiment, the longitudinal extent of the second conductive tube 72B is about the same as (or even less than) the longitudinal extent of the glass body 48. In this way, sensor 10 is at least partially bendable at the longitudinal portion of the sensor that does not include the glass body 48 or the conductive tube 72B. Although the illustrated embodiment includes the first conductive tube 72A, in other embodiments the first conductive tube may be omitted, such that the solution ground assembly 22 includes only the second conductive tube 72B. In still other embodiments, an electrically conductive tube may be omitted.

Referring to FIG. 5, in one example, the longitudinal extent of the second electrically conductive tube 72B is less than ¾ the length L1 of the housing 12. In other words, a first end 73 of the second electrically conductive tube 72B does not extend to (i.e., is spaced apart longitudinally from) a first quarter-length QL1 of the housing 12 as measured from the first longitudinal end 14A of the housing. In another embodiment, the longitudinal extent of the second electrically conductive tube 72B is less than ½ the length L1 of the housing 12. In other words, the first end 73 of the second electrically conductive tube 72B does not extend to (i.e., is spaced apart longitudinally from) a second quarter-length QL2 (i.e., mid-length) of the housing 12 as measured from the first longitudinal end 14A of the housing. In yet another embodiment, the longitudinal extent of the second electrically conductive tube 72B is less than or equal to ⅓ the length of the housing 12. In other words, the first end 73 of the second electrically conductive tube 72B would not extend to (i.e., is spaced apart longitudinally from) a second one-third length OTL2 of the housing 12 as measured from the first longitudinal end 14A of the housing. In another embodiment, the longitudinal extent of the second electrically conductive tube 72B is less than ¼ the length L1 of the housing 12. In other words, the first end 73 of the second electrically conductive tube 72B does not extend to (i.e., is spaced apart longitudinally from) a third quarter-length QL3 of the housing 12 as measured from the first longitudinal end 14A of the housing.

Figure 7:
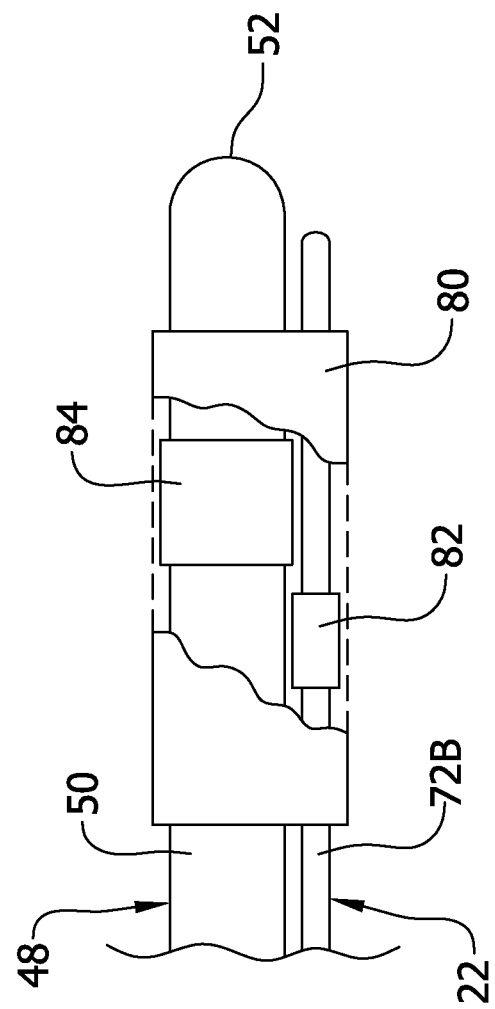
FIG. 7 is a fragmentary elevation of the sensor of FIG. 1 with a housing removed.

In the illustrated embodiment (FIG. 7), the glass body 48 is anchored to the solution ground assembly 22 at the electrically conductive second tube 72B to further inhibit displacement of the glass body 48 relative to the housing 12 during thermal expansion and contraction of the housing. In the illustrated embodiment, the glass body 48 is anchored to the ground assembly 22 by heat shrink tubing 80. Because the surfaces of the solution assembly 22 and the glass body 48 are relatively smooth and may not provide adequate frictional engagement with the heat shrink tubing 80, additional heat shrink tubing 82, 84 is first applied to the solution ground assembly 22 and the glass body. The anchoring heat shrink tubing 80 is then applied over the heat shrink tubing 82, 84 to anchor the glass body 48 to the solution ground assembly. Other ways of anchoring the glass body 48 to the solution ground assembly 22 are possible. Moreover, in some embodiments the glass body 48 may not be anchored to the solution ground assembly 22.

When assembling the sensor 10, the measuring half-cell assembly 20 and the solution ground assembly 22 are inserted in the second seal 30B, and the heat shrink tubing 80, 82, 84 is applied to the components, as disclosed above. This assembly is inserted into the reference electrolyte solution through the second longitudinal end 14B (e.g., the bottom) of the housing 12.

In general, it is believed that the sensor 10 disclosed above has a number of advantages. For example, it is believed that the sensor 10 will be able to withstand shock without failing or breaking, such as when the sensor is dropped. The sensor 10 can withstand moderate deflection (i.e., bending) along its length without failing or breaking. The sensor 10 can withstand stresses induced by unmatched coefficients of thermal linear expansion of the glass body 48 of the measuring half-cell assembly 20 and the housing 12. The measuring half-cell assembly 20 and the solution ground assembly 22 are modular or universal in that the same half-cell assembly and solution ground assembly can be used for sensors of various lengths. Only the lengths of the wires would need to be changed. Moreover, the first seal 30A has a simpler design since the glass body 48 does not pass through the seal.

Drop Testing

Figure 8:
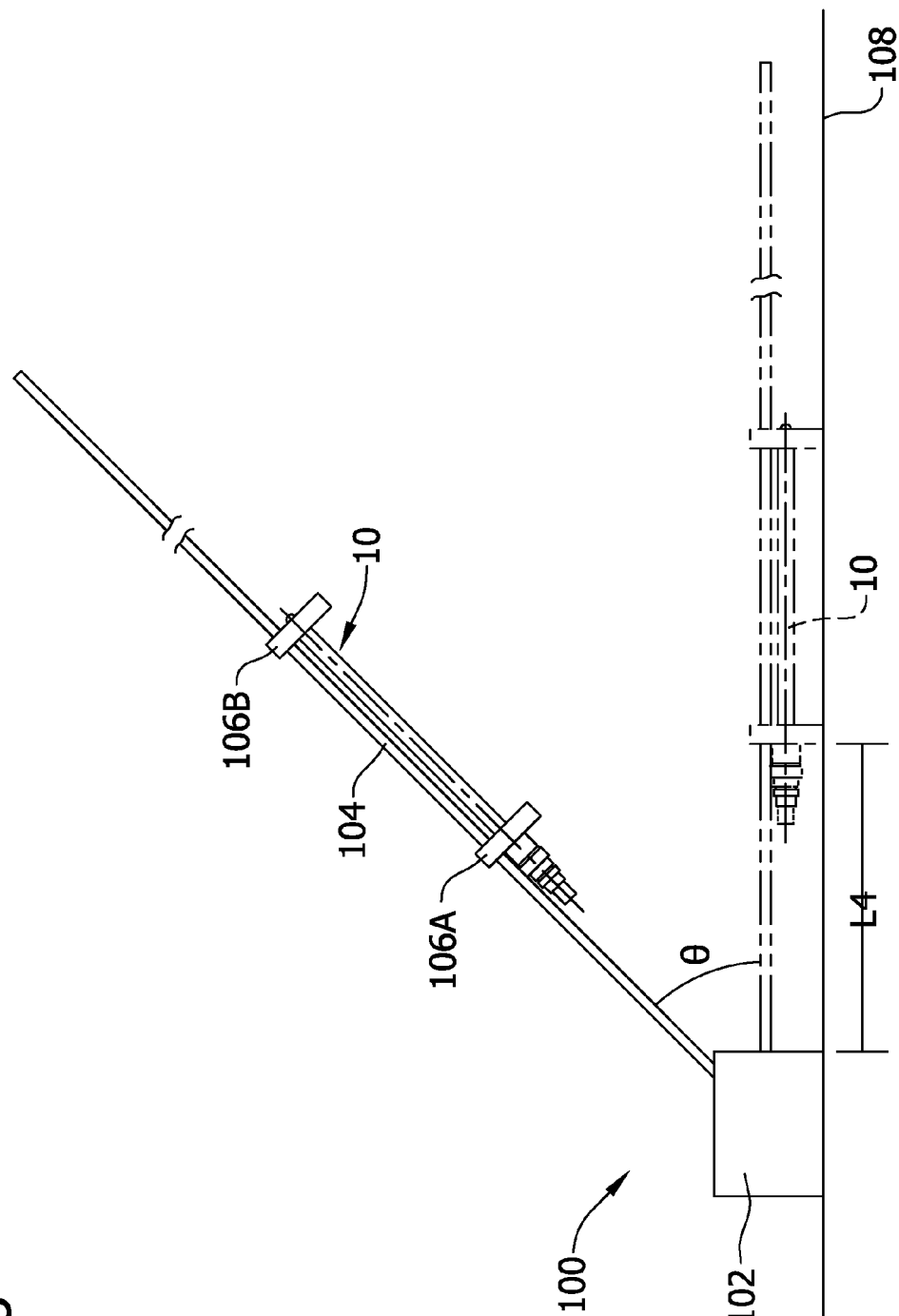
FIG. 8 is an elevation of a testing fixture for drop testing.

Turning now to FIG. 8, a drop testing apparatus for testing the impact resistance of a potentiometric sensor 10 is generally indicated at reference number 100. The testing apparatus 100 includes a hinged release mechanism 102, a drop arm 104 and sensor mounting brackets 106A and 106B. During drop testing, sensors 10, conforming to the above-described embodiment of the invention, were installed on the drop arm 104 with mounting brackets 106A and 106B. The impact resistance of sensors constructed according to certain aspects of this invention was tested by dropping the sensors in a repeatable fashion using the testing apparatus 100. As shown in more detail in the charts set out below, sensors 10 with PEEK housings 12 of lengths of 120 mm, 225 mm, 360 mm, and 425 mm were dropped from varying drop angles θ while attached to the drop arm 104 at varying drop lengths L4. To measure the performance of the sensors after undergoing the impact of each drop from angle θ and length L4, the sensor response to a solution of pH 7 was compared with a baseline measurement of the sensor response to a solution of pH 7 prior to being dropped. When the sensor output an after-drop response substantially identical to the before-drop response, the sensor was awarded a passing score for a given angle θ and length L4.

Table 1, below, shows the response of sensor 10 with a 120 mm housing 12 to a series of drop tests. The sensor 10 was dropped one time for a given length L4 at angles θ ranging from 10° to 80° in 10° increments. For each angle θ, the sensor was tested at a drop length of 3", 21", 27", and 33". As shown below, the 120 mm sensor 10 showed no loss of performance after undergoing these tests.

TABLE 1

Single Drop Response of 120 mm Sensor

| Drop Angle vs. Drop length | 3" | 21" | 27" | 33" |
| --- | --- | --- | --- | --- |
| 10° | Pass | Pass | Pass | Pass |
| 20° | Pass | Pass | Pass | Pass |
| 30° | Pass | Pass | Pass | Pass |
| 40° | Pass | Pass | Pass | Pass |
| 50° | Pass | Pass | Pass | Pass |
| 60° | Pass | Pass | Pass | Pass |
| 70° | Pass | Pass | Pass | Pass |
| 80° | Pass | Pass | Pass | Pass |

Table 2 shows the response of sensor 10 with a 225 mm housing 12 to a series of drop tests. As above, for a given drop length, the 225 mm sensor 10 was dropped one time each at angles θ ranging from 10° to 80° in 10° increments. For each angle θ, the sensor was tested at a drop length of 3", 21", 27", and 33". As shown below, the 225 mm sensor 10 showed no loss of performance after undergoing these tests.

TABLE 2

Single Drop Response of 225 mm Sensor

| Drop Angle vs. Drop length | 3" | 21" | 27" | 33" |
| --- | --- | --- | --- | --- |
| 10° | Pass | Pass | Pass | Pass |
| 20° | Pass | Pass | Pass | Pass |

TABLE 2-continued

Single Drop Response of 225 mm Sensor

| Drop Angle vs. Drop length | 3" | 21" | 27" | 33" |
|---|---|---|---|---|
| 30° | Pass | Pass | Pass | Pass |
| 40° | Pass | Pass | Pass | Pass |
| 50° | Pass | Pass | Pass | Pass |
| 60° | Pass | Pass | Pass | Pass |
| 70° | Pass | Pass | Pass | Pass |
| 80° | Pass | Pass | Pass | Pass |

Table 3 shows the response of sensor 10 with a 360 mm housing 12 to a series of drop tests. As above, for a given drop length L4, the 360 mm sensor 10 was dropped one time each at angles θ ranging from 10° to 80° in 10° increments. For each angle θ, the sensor was tested at a drop length of 3", 21", and 27". Due to the constraint of the length of the drop arm 104, the 360 mm sensor housing 12 could not be tested at a drop length of 33". As shown below, the 360 mm sensor 10 showed no loss of performance after undergoing these tests.

TABLE 3

Single Drop Response of 360 mm Sensor

| Drop Angle vs. Drop length | 3" | 21" | 27" |
|---|---|---|---|
| 10° | Pass | Pass | Pass |
| 20° | Pass | Pass | Pass |
| 30° | Pass | Pass | Pass |
| 40° | Pass | Pass | Pass |
| 50° | Pass | Pass | Pass |
| 60° | Pass | Pass | Pass |

TABLE 3-continued

Single Drop Response of 360 mm Sensor

| Drop Angle vs. Drop length | 3" | 21" | 27" |
|---|---|---|---|
| 70° | Pass | Pass | Pass |
| 80° | Pass | Pass | Pass |

Table 4 shows the response of sensor 10 with a 425 mm housing 12 to a series of drop tests. As above, for a given drop length L4, the 425 mm sensor 10 was dropped one time each at angles θ ranging from 10° to 80° in 10° increments. For each angle θ, the sensor was tested at a drop length of 3", 21", and 27". Due to the constraint of the length of the drop arm 104, the 425 mm sensor 10, like the 360 mm sensor above, could not be tested at a drop length of 33". As shown below, the 425 mm sensor 10 showed no loss of performance after undergoing these tests.

TABLE 4

Single Drop Response of 425 mm Sensor

| Drop Angle vs. Drop length | 3" | 21" | 27" |
|---|---|---|---|
| 10° | Pass | Pass | Pass |
| 20° | Pass | Pass | Pass |
| 30° | Pass | Pass | Pass |
| 40° | Pass | Pass | Pass |
| 50° | Pass | Pass | Pass |
| 60° | Pass | Pass | Pass |
| 70° | Pass | Pass | Pass |
| 80° | Pass | Pass | Pass |

Table 5 shows the response of a sensor 10 with a 120 mm housing 12 to another series of drop tests. Unlike above, for a given drop length L4, the 120 mm sensor 10 was dropped three times at each angle ranging from 10° to 80° in 10° increments. For each angle θ, the sensor was tested for its triple drop response at a drop length of 6", 18", 24", 30", 36", and 39". To test the 120 mm sensor 10's triple drop durability, its response was measured after each of a first, second, and third drop at a given drop angle θ and drop length L4. As shown below, the 120 mm sensor 10 showed no loss of performance after undergoing these tests. To help consolidate information, in each of the subsequent tables, a passing response will be indicated by the letter P and a failing response will be indicated by the letter F.

TABLE 5

Triple Drop Response of 120 mm Sensor

| Drop Angle vs. Drop Length | 6" | | | 18" | | | 24" | | | 30" | | | 36" | | | 39" | | |
|---|---|---|---|---|---|---|---|---|---|---|---|---|---|---|---|---|---|---|
| Test # | 1 | 2 | 3 | 1 | 2 | 3 | 1 | 2 | 3 | 1 | 2 | 3 | 1 | 2 | 3 | 1 | 2 | 3 |
| 10° | P | P | P | P | P | P | P | P | P | P | P | P | P | P | P | P | P | P |
| 20° | P | P | P | P | P | P | P | P | P | P | P | P | P | P | P | P | P | P |
| 30° | P | P | P | P | P | P | P | P | P | P | P | P | P | P | P | P | P | P |
| 40° | P | P | P | P | P | P | P | P | P | P | P | P | P | P | P | P | P | P |
| 50° | P | P | P | P | P | P | P | P | P | P | P | P | P | P | P | P | P | P |
| 60° | P | P | P | P | P | P | P | P | P | P | P | P | P | P | P | P | P | P |
| 70° | P | P | P | P | P | P | P | P | P | P | P | P | P | P | P | P | P | P |
| 80° | P | P | P | P | P | P | P | P | P | P | P | P | P | P | P | P | P | P |

Table 6 shows the response of a sensor 10 with a 225 mm housing 12 to another series of triple drop tests. As in Table 5 above, for a given drop length L4, the 225 mm sensor 10 was dropped three times at each angle θ ranging from 10° to 80° in 10° increments. For each angle θ, the sensor was tested for its triple drop response at a drop length of 6", 18", 24", 30", and 36". Due to the constraint of the length of the drop arm 104, the 225 mm sensor could not be tested at a drop length of 39". To test the 225 mm sensor 10's triple drop durability, its response was measured after each of a first, second, and third drop at a given drop angle θ and drop length L4. As shown below, the 225 mm sensor 10 showed no loss of performance after undergoing these tests.

TABLE 6

Triple Drop Response of 225 mm Sensor

| Drop Angle vs. Drop Length | 6" | | | 18" | | | 24" | | | 30" | | | 36" | | |
|---|---|---|---|---|---|---|---|---|---|---|---|---|---|---|---|
| Test # | 1 | 2 | 3 | 1 | 2 | 3 | 1 | 2 | 3 | 1 | 2 | 3 | 1 | 2 | 3 |
| 10° | P | P | P | P | P | P | P | P | P | P | P | P | P | P | P |
| 20° | P | P | P | P | P | P | P | P | P | P | P | P | P | P | P |
| 30° | P | P | P | P | P | P | P | P | P | P | P | P | P | P | P |
| 40° | P | P | P | P | P | P | P | P | P | P | P | P | P | P | P |
| 50° | P | P | P | P | P | P | P | P | P | P | P | P | P | P | P |
| 60° | P | P | P | P | P | P | P | P | P | P | P | P | P | P | P |
| 70° | P | P | P | P | P | P | P | P | P | P | P | P | P | P | P |
| 80° | P | P | P | P | P | P | P | P | P | P | P | P | P | P | P |

Table 7 shows the response of a sensor 10 with a 360 mm housing 12 to another series of triple drop tests. As in Tables 5 and 6 above, for a given drop length L4, the 360 mm sensor 10 was dropped three times at each angle θ ranging from 10° to 80° in 10° increments. For each angle θ, the sensor was tested for its triple drop response at a drop length of 6", 18", 24", and 30". Due to the constraint of the length of the drop arm 104, the 360 mm sensor could not be tested at drop lengths of 36" and 39". To test the 360 mm sensor 10's triple drop durability, its response was measured after each of a first, second, and third drop at a given drop angle θ and drop length L4. As shown below, the 360 mm sensor 10 showed no loss of performance after undergoing these tests.

TABLE 7

Triple Drop Response of 360 mm Sensor

| Drop Angle vs. Drop Length | 6" | | | 18" | | | 24" | | | 30" | | |
|---|---|---|---|---|---|---|---|---|---|---|---|---|
| Test # | 1 | 2 | 3 | 1 | 2 | 3 | 1 | 2 | 3 | 1 | 2 | 3 |
| 10° | P | P | P | P | P | P | P | P | P | P | P | P |
| 20° | P | P | P | P | P | P | P | P | P | P | P | P |
| 30° | P | P | P | P | P | P | P | P | P | P | P | P |
| 40° | P | P | P | P | P | P | P | P | P | P | P | P |
| 50° | P | P | P | P | P | P | P | P | P | P | P | P |
| 60° | P | P | P | P | P | P | P | P | P | P | P | P |
| 70° | P | P | P | P | P | P | P | P | P | P | P | P |
| 80° | P | P | P | P | P | P | P | P | P | P | P | P |

Table 8 shows the response of a sensor 10 with a 425 mm housing 12 to another series of triple drop tests. As in Tables 5-7 above, for a given drop length L4, the 425 mm sensor 10 was dropped three times at each angle θ ranging from 10° to 80° in 10° increments. For each angle θ, the sensor was tested for its triple drop response at a drop length of 6", 18", and 24". Due to the constraint of the length of the drop arm 104, the 425 mm sensor could not be tested at drop lengths of 30", 36", and 39". To test the 425 mm sensor 10's triple drop durability, its response was measured after each of a first, second, and third drop at a given drop angle θ and drop length L4. As shown below, the 425 mm sensor 10 showed no loss of performance after undergoing these tests.

TABLE 8

Triple Drop Response of 425 mm Sensor

| Drop Angle vs. Drop Length | 6" | | | 18" | | | 24" | | |
|---|---|---|---|---|---|---|---|---|---|
| Test # | 1 | 2 | 3 | 1 | 2 | 3 | 1 | 2 | 3 |
| 10° | P | P | P | P | P | P | P | P | P |
| 20° | P | P | P | P | P | P | P | P | P |
| 30° | P | P | P | P | P | P | P | P | P |
| 40° | P | P | P | P | P | P | P | P | P |
| 50° | P | P | P | P | P | P | P | P | P |
| 60° | P | P | P | P | P | P | P | P | P |
| 70° | P | P | P | P | P | P | P | P | P |
| 80° | P | P | P | P | P | P | P | P | P |

As can be seen from Tables 1-8 above, the performance of potentiometric sensors constructed according to principles of the present invention is substantially immune to the impact of being dropped, irrespective of the length of the sensor. Thus, in some embodiments, the present invention includes a potentiometric sensor wherein the measuring half-cell assembly and the housing remain intact and in operable condition when the potentiometric sensor is dropped from a height. In many embodiments, the measuring half-cell assembly and the housing remain intact and in operable condition when dropped from a height in a range of about three inches to about thirty-nine inches. In some embodiments, the measuring half-cell assembly and the housing remain intact and in operable condition when dropped from a height in a range of about twenty-four inches to about thirty-nine inches. Other embodiments may remain intact after being dropped from other heights without departing from the scope of the present invention. In any case, as demonstrated in the results of the experiments set out in Tables 1-8, potentiometric sensors constructed according to the principles of the present invention may remain operable after experiencing the impact of being dropped from a height.

Fit Testing

The following testing was performed on sensors 10 having the design shown throughout the drawings and described above. The sensors 10 tested had PEEK housings 12 with lengths of 120 mm, 225 mm, 360 mm, and 425 mm. Three sensors 10 of each length were tested, as described below and illustrated in FIGS. 9(a)-9(d). The sensors 10 were tested at the beginning and at the end, following all of the tests discussed below. Interim testing was performed between tests to verify that the sensor 10 was functioning and working properly. As shown best in FIG. 9(a), the sensors 10 were inserted into appropriately sized process line insertion assemblies 200 that are well understood in the art. Once inserted, the sensors 10 were fully installed in their assemblies 200 at their maximum insertion length (FIG. 9(b)). Thereafter, each sensor 10 was removed from its insertion assembly 200 (FIGS. 9(c) and 9(d)). One sensor 10 of each length was installed in an appropriate process line insertion assembly 200. Each sensor 10 was cycled 5 times from minimum to maximum insertion length and was removed after each cycle and tested in pH 7 buffer. None of the tested sensors broke or failed to operate after the testing. Accordingly, in certain embodiments, the present invention includes potentiometric sensors whose measuring half-cell assembly and housing remain intact and in operable condition after being inserted into and removed from a process fluid line insertion assembly at least five times.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A potentiometric sensor comprising:
   an elongate non-glass, non-metal housing having opposite first and second longitudinal ends and a length extending between the first and second longitudinal ends, the housing defining a lumen extending along the length of the housing; and
   a measuring half-cell assembly received in the lumen of the housing and secured to the housing, the measuring half-cell assembly including a glass body having opposite first and second longitudinal ends and a length extending between the first and second ends of the glass body, wherein the second longitudinal end of the glass body is adjacent the second longitudinal end of the housing and a longitudinal extent of the glass body is less than the length of the housing;
   wherein the sensor is at least partially bendable along a longitudinal portion that does not include the glass body.

2. The potentiometric sensor of claim 1 wherein the longitudinal extent of the glass body is less than three-quarters the length of the housing.

3. The potentiometric sensor of claim 2 wherein the longitudinal extent of the glass body is less than one-half the length of the housing.

4. The potentiometric sensor of claim 3 wherein the longitudinal extent of the glass body is less than one-third the length of the housing.

5. The potentiometric sensor of claim 4 wherein the longitudinal extent of the glass body is less than one-fourth the length of the housing.

6. The potentiometric sensor of claim 1 wherein the glass body is secured to the housing at a single longitudinal portion of the glass body so that the glass body generally moves with the housing during thermal linear expansion of the housing.

7. The potentiometric sensor of claim 1 wherein the measuring half-cell assembly further includes a lead wire extending through the lumen to the glass body, a reference wire within the glass body, and a seal in the glass body, the lead wire and the reference wire being electrically connected in the seal.

8. The potentiometric sensor of claim 1 wherein the housing comprises a plastic material.

9. A potentiometric sensor comprising:
   an elongate non-glass, non-metal housing having opposite first and second longitudinal ends and a length extending between the first and second longitudinal ends, the housing defining a lumen extending along the length of the housing;
   a measuring half-cell assembly received in the lumen of the housing, the measuring half-cell assembly including a glass body having opposite first and second longitudinal ends and a length extending between the first and second ends of the glass body, wherein the glass body is secured to the housing at a single longitudinal portion of the glass body so that the glass body generally moves with the housing during thermal linear expansion of the housing; and
   a seal positioned at the single longitudinal portion of the glass body for inhibiting the ingress and egress of fluid into and out the lumen and securing the housing to the single longitudinal portion of the glass body, the seal comprising an electrically conductive end cap that is electrically connected to a wire and a process fluid.

10. The potentiometric sensor of claim 9 further comprising another seal adjacent the first longitudinal end of the housing for inhibiting the ingress and egress of fluid into and out the lumen.

11. The potentiometric sensor of claim 10 wherein the first end of the glass body is free from securement to said other seal and is spaced apart from said other seal along the length of the housing.

12. The potentiometric sensor of claim 9 wherein the measuring half-cell assembly further includes a lead wire extending through the lumen to the glass body, a reference wire within the glass body, and a glass body seal in the glass body, the lead wire and the reference wire being electrically connected in the glass body seal.

13. The potentiometric sensor of claim 9 further comprising a solution ground assembly and a heat shrinking tube, the heat shrinking tube disposed around a portion of the glass body and a portion of the solution ground assembly to hold said portion of the glass body in place with respect to said portion of the solution ground assembly.

14. A potentiometric sensor comprising:
   an elongate non-glass, non-metal housing having opposite first and second longitudinal ends and a length extending between the first and second longitudinal ends, the housing defining a lumen extending along the length of the housing;
   a first seal adjacent the first longitudinal end of the housing for inhibiting the ingress and egress of fluid into and out the lumen;
   a second seal spaced apart from the first seal along the length of the housing, the second seal being adjacent the second longitudinal end of the housing for inhibiting the ingress and egress of fluid into and out of the lumen; and a measuring half-cell assembly received in the lumen of the housing, the measuring half-cell assembly including a glass body having opposite first and second longitudinal ends and a length extending between the first and second ends of the glass body that is less than the length of the housing, the measuring half-cell assembly further including a lead wire extending through the lumen to the glass body, a reference wire within the glass body, and a glass body seal in the glass body, the lead wire and the reference wire being electrically connected in the glass body seal.

15. The potentiometric sensor of claim 14 wherein the second longitudinal end of the glass body is adjacent the second longitudinal end of the housing and a longitudinal extent of the glass body is less than the length of the housing.

16. The potentiometric sensor of claim 14 wherein the glass body is secured to the housing at a single longitudinal portion of the glass body so that the glass body generally moves with the housing during thermal linear expansion of the housing.

17. The potentiometric sensor of claim 14 wherein the glass body seal comprises longitudinally spaced first and second glass body seals and electrically non-conductive material disposed between the first and second glass body seals and wherein the lead wire and the reference wire are electrically connected in the non-conductive material.

* * * * *